US009181146B2

(12) United States Patent
Iaccino et al.

(10) Patent No.: US 9,181,146 B2
(45) Date of Patent: Nov. 10, 2015

(54) PROCESS FOR THE PRODUCTION OF XYLENES AND LIGHT OLEFINS

(75) Inventors: Larry L. Iaccino, Seabrook, TX (US);
James R. Lattner, LaPorte, TX (US);
Glenn C. Wood, Houston, TX (US);
Surbhi Jain, Houston, TX (US);
Stephen M. Davis, Humble, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 10 days.

(21) Appl. No.: 13/465,721

(22) Filed: May 7, 2012

(65) Prior Publication Data
US 2013/0296621 A1 Nov. 7, 2013

(51) Int. Cl.
*C07C 1/24* (2006.01)
*C07C 2/86* (2006.01)
*C10G 29/20* (2006.01)
*C10G 35/00* (2006.01)
*C10G 57/00* (2006.01)
*C10G 9/00* (2006.01)
*C10G 9/36* (2006.01)
*C10G 11/00* (2006.01)

(52) U.S. Cl.
CPC ............... *C07C 2/864* (2013.01); *C10G 9/005* (2013.01); *C10G 9/36* (2013.01); *C10G 11/00* (2013.01); *C10G 29/205* (2013.01); *C10G 35/00* (2013.01); *C10G 57/005* (2013.01); *C10G 2300/1092* (2013.01); *C10G 2300/1096* (2013.01); *C10G 2400/30* (2013.01)

(58) Field of Classification Search
USPC ......... 585/708, 752, 709, 710, 717, 648, 653, 585/470, 310, 319, 323, 483, 400
See application file for complete search history.

(56) References Cited

U.S. PATENT DOCUMENTS

| | | | |
|---|---|---|---|
| 2,415,272 A | 2/1947 | Benedict et al. | |
| 3,409,540 A | 11/1968 | Gould et al. | |
| 3,862,898 A | 1/1975 | Boyd et al. | |
| 3,894,934 A * | 7/1975 | Owen et al. | 208/78 |
| 4,053,388 A | 10/1977 | Bailey | |
| 4,058,450 A | 11/1977 | Le Page et al. | |
| 4,058,454 A | 11/1977 | Asselin | |
| 4,078,990 A | 3/1978 | Brennan et al. | |
| 4,257,871 A | 3/1981 | Wernicke et al. | |
| 4,980,053 A | 12/1990 | Li et al. | |
| 5,043,502 A | 8/1991 | Martindale et al. | |
| 5,232,675 A | 8/1993 | Shu et al. | |
| 5,326,465 A | 7/1994 | Yongqing et al. | |
| 5,358,918 A | 10/1994 | Yukang et al. | |
| 5,380,690 A | 1/1995 | Zhicheng et al. | |
| 5,932,777 A | 8/1999 | Sughrue et al. | |
| 6,077,984 A | 6/2000 | Drake et al. | |
| 6,080,698 A | 6/2000 | Zhang et al. | |
| 6,114,592 A | 9/2000 | Gajda et al. | |
| 6,153,089 A | 11/2000 | Das et al. | |
| 6,210,562 B1 | 4/2001 | Xie et al. | |
| 6,211,104 B1 | 4/2001 | Shi et al. | |
| 6,342,153 B1 | 1/2002 | Guan et al. | |
| 6,420,621 B2 | 7/2002 | Sha et al. | |
| 6,423,879 B1 | 7/2002 | Brown et al. | |
| 6,504,073 B1 | 1/2003 | Ushio et al. | |
| 6,635,792 B2 | 10/2003 | Choi et al. | |
| 6,740,788 B1 | 5/2004 | Maher et al. | |
| 7,119,239 B2 | 10/2006 | Johnson et al. | |
| 7,153,478 B2 | 12/2006 | Xu et al. | |
| 7,176,339 B2 | 2/2007 | Iaccino et al. | |
| 7,179,434 B1 | 2/2007 | Maher et al. | |
| 7,288,687 B1 | 10/2007 | Frey et al. | |
| 7,297,831 B2 | 11/2007 | Lee et al. | |
| 7,301,063 B2 | 11/2007 | Choi et al. | |
| 7,396,967 B2 * | 7/2008 | Iaccino et al. | 585/323 |
| 7,553,791 B2 | 6/2009 | McMinn et al. | |
| 7,563,358 B2 | 7/2009 | Stavens et al. | |
| 7,578,929 B2 | 8/2009 | Stell et al. | |
| 7,601,311 B2 | 10/2009 | Casey et al. | |
| 7,629,498 B2 * | 12/2009 | Brown et al. | 585/467 |

(Continued)

FOREIGN PATENT DOCUMENTS

| | | |
|---|---|---|
| AU | 776 247 | 9/2004 |
| EP | 0 136 072 | 4/1985 |
| EP | 0136072 | 4/1985 |
| EP | 1 068 166 | 3/2004 |
| EP | 1068166 | 3/2004 |
| KR | 10-0632571 | 10/2006 |
| WO | WO 97/45387 | 12/1997 |
| WO | WO 01/79383 | 10/2001 |
| WO | 02/44306 | 6/2002 |
| WO | WO 2004/005432 | 1/2004 |
| WO | WO 2006/068800 | 6/2006 |
| WO | 2007-108573 | 9/2007 |
| WO | WO 2007/108573 | 9/2007 |
| WO | WO 2010/138504 | 12/2010 |
| WO | WO 2012/015541 | 2/2012 |

OTHER PUBLICATIONS

U.S. Appl. No. 61/421,917, filed Dec. 10, 2010, Ellrich et al.

(Continued)

*Primary Examiner* — In Suk Bullock
*Assistant Examiner* — Sharon Pregler

(57) ABSTRACT

In a hydrocarbon upgrading process, a hydrocarbon feed is treated in at least one of a steam cracker, catalytic cracker, coker, hydrocracker, and reformer under suitable conditions to produce a first stream comprising olefinic and aromatic hydrocarbons. A second stream composed mainly of $C_4$ to $C_{12}$ olefinic and aromatic hydrocarbons is recovered from the first stream and at least part of the second stream is contacted with a catalyst in the absence of added hydrogen under reaction conditions including a temperature of about 450° C. to about 70° C. effective to dealkylate, transalkylate, crack and aromatize components of the second stream to produce a third stream having an increased benzene and/or toluene content compared with the second stream and a $C_3$– olefin by-product. The $C_3$– olefin by-product and a fourth stream comprising toluene are then recovered from the third stream.

28 Claims, 1 Drawing Sheet

(56) References Cited

U.S. PATENT DOCUMENTS

| | | |
|---|---|---|
| 7,727,490 B2 | 6/2010 | Zhou |
| 7,923,399 B2 | 4/2011 | Long et al. |
| 7,939,702 B2 | 5/2011 | Choi et al. |
| 7,972,498 B2 | 7/2011 | Buchanan et al. |
| 8,183,424 B2 | 5/2012 | Levin et al. |
| 2001/0053868 A1 | 12/2001 | Chester et al. |
| 2003/0105372 A1 | 6/2003 | Feng et al. |
| 2003/0116471 A1 | 6/2003 | Zhang et al. |
| 2004/0015027 A1 | 1/2004 | Iaccino et al. |
| 2004/0049093 A1 | 3/2004 | Cheung et al. |
| 2005/0020867 A1 | 1/2005 | Xie et al. |
| 2005/0209495 A1 | 9/2005 | McCoy et al. |
| 2006/0194996 A1 | 8/2006 | Umansky et al. |
| 2008/0051615 A1 | 2/2008 | Stavens et al. |
| 2008/0249345 A1 | 10/2008 | Kinn et al. |
| 2009/0000988 A1 | 1/2009 | Brown et al. |
| 2010/0040517 A1 | 2/2010 | Brown et al. |
| 2012/0149958 A1 | 6/2012 | Ellrich et al. |

OTHER PUBLICATIONS

Baillie et al., "*FCC Catalysts: Now Rare Earth Free,*" Hydrocarbon Engineering, Mar. 2011, vol. 16, No. 3, pp. 33-36.

* cited by examiner

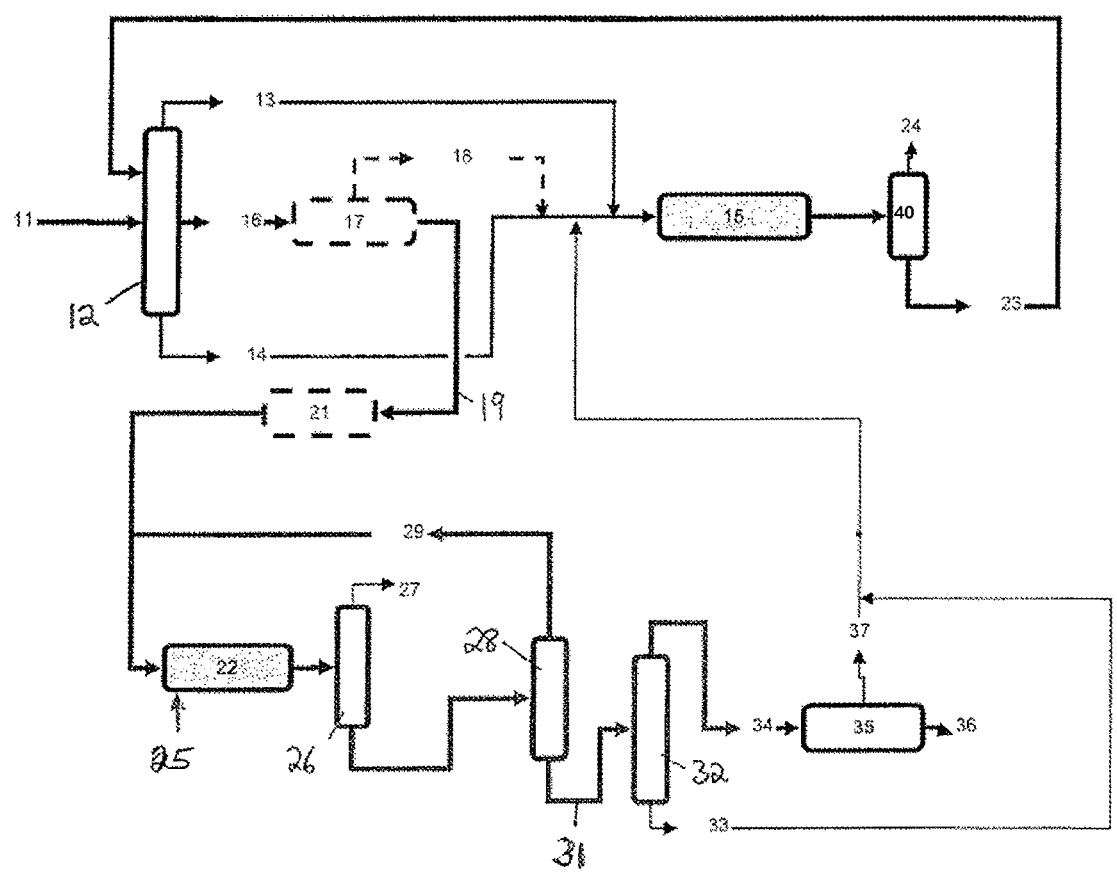

PROCESS FOR THE PRODUCTION OF XYLENES AND LIGHT OLEFINS

CROSS REFERENCE TO RELATED PATENT APPLICATIONS

This application is related to U.S. Ser. No. 13/303,855, filed Nov. 23, 2011, which claims the benefit of and priority to U.S. Ser. No. 61/421,917, Dec. 10, 2010, both of which are fully incorporated herein by reference.

FIELD OF THE INVENTION

The invention relates to a process for the production of xylenes and light ($C_3-$) olefins from diverse olefinic feedstocks.

BACKGROUND OF THE INVENTION

Xylene isomers find wide and varied application. They are especially valuable as intermediates in chemical processes. By way of example, para-xylene (PX) is a feedstock for terephthalic acid, which finds use in the manufacture of polyester fibers and films, meta-xylene (MX) is used in the manufacture of dyes, and ortho-xylene (OX) is used as a feedstock for phthalic anhydride, which finds use in the manufacture of plasticizers. PX is currently the most valuable of the xylene isomers and, although research related to obtaining (e.g., producing or purifying) PX is too voluminous to mention, there is still intensive research in the area.

There are many possible feeds currently used to obtain PX. The majority of para-xylene produced today comes from catalytic reforming, which involves dehydrogenation and dehydrocyclization of naphtha feedstocks. The effluent of the reforming process, known as reformate, is rich in aromatics, particularly benzene, toluene and mixed xylenes (BTX), and is used as feedstock to aromatics plants. Processes exist to increase the yield of para-xylene over the equilibrium mixture in the reformate, including selective toluene disproportionation and selective methylation of benzene and/or toluene with methanol.

Recently, significant research has focused on finding alternative sources and methods for producing BTX and particularly para-xylene. For example, although steam cracking, or pyrolysis, is the preferred method of producing light olefins (ethylene, propylene, and butenes) from heavier hydrocarbon feedstocks, the process also generates a by-product termed pyrolysis gasoline, steam cracked naphtha (SCN) or pygas. Pygas is a complex mixture of $C_6$ to $C_{10}+$ hydrocarbons that is rich in aromatics, particularly benzene and toluene, but also contains $C_8$, $C_9$, and $C_{10}+$ aromatics. Similarly, catalytic cracking, particularly fluid catalytic cracking (FCC), in addition to producing fuels and light olefins, generates a $C_6$ to $C_{10+}$ aromatic rich stream which is similar to pygas and is generally known as cat naphtha. These processes also produce $C_4$ and $C_5$ olefinic streams which have some utility, but tend to be of lower value than aromatic products and lighter olefins (ethylene and propylene). There is significant interest in developing methods of upgrading alternate feed sources, such as pygas and cat naphtha, to increase the yield of ethylene, propylene, BTX; and preferably para-xylene and propylene. There are some processes proposed to upgrade these streams to produce BTX, but they consume expensive $H_2$ and co-produce lower value light saturates rather than higher value light olefins. Olefinic streams are also recognized to contain di-olefins and acetylenes.

For example, U.S. Pat. No. 6,635,792 discloses a process for producing BTX and liquefied petroleum gas (LPG) from a hydrocarbon feedstock having boiling points of 30° C.-250° C., such as reformate and pyrolysis gasoline. In the process, aromatic components in the hydrocarbon feedstock are converted to BTX-enriched components in the liquid phase through hydrodealkylation and/or transalkylation, and non-aromatic components are converted to LPG-enriched gaseous materials through hydrocracking. The process employs a catalyst comprising platinum/tin or platinum/lead on mordenite, zeolite beta or ZSM-5 and is said to have the advantage of avoiding the need of a solvent extraction step to remove aliphatic compounds from the hydrocarbon feedstock. U.S. Pat. Nos. 7,297,831 and 7,301,063 disclose similar processes.

U.S. Pat. No. 7,176,339 discloses a process for producing xylenes from reformate, which process comprises: (a) providing a reformate containing hydrogen, $C_1$ to $C_5$ hydrocarbons, $C_6$ to $C_7$ hydrocarbons comprising benzene, toluene or mixtures thereof, and $C_8+$ hydrocarbons; (b) removing at least a portion of said hydrogen from said reformate to produce a product containing $C_6$ to $C_7$ hydrocarbons comprising benzene, toluene or mixtures thereof, and $C_8+$ hydrocarbons; and (c) methylating at least a portion of the benzene, toluene, or mixtures thereof present in said product with a methylating agent under vapor phase conditions and in the presence of a catalyst effective for the methylation to produce a resulting product having a higher para-xylene content than the reformate, wherein the catalyst comprises a zeolite-bound-zeolite catalyst and/or a selectivated zeolite and the zeolite comprises ZSM-5. One of the problems alleged to be overcome by this process is the need for an expensive aromatics extraction step to separate $C_6$ to $C_7$ aromatics from the $C_6$ to $C_7$ aliphatics after removal of the hydrogen and $C_1$ to $C_5$ hydrocarbons. A similar process is disclosed in U.S. Pat. No. 7,629,498.

U.S. Pat. No. 7,563,358 discloses a process for producing BTX-enriched product from a hydrocarbon feed comprising: (a) $C_6+$ non-aromatic cyclic hydrocarbons; (b) $C_8+$ single-ring aromatic hydrocarbons having at least one alkyl group containing two or more carbon atoms; and (c) $C_9+$ single-ring aromatic hydrocarbons having at least three methyl groups, by contacting the feed in the presence of hydrogen with a catalyst comprising at least one Group VIII metal and a large or intermediate pore molecular sieve having an alpha value, before incorporation of the Group VIII metal, from about 2 to less than 100 under conditions sufficient for (i) forming aromatic hydrocarbons from $C_6+$ non-aromatic cyclic hydrocarbons; (ii) dealkylating $C_8+$ single-ring aromatic hydrocarbons having at least one alkyl group containing two or more carbon atoms; (iii) transalkylating $C_9+$ single-ring aromatic hydrocarbons having at least three methyl groups; and (iv) disproportionating toluene, to produce a product containing an increased amount of BTX compared to the feed. A preferred hydrocarbon feed is steam cracked naphtha.

In U.S. Application Ser. No. 61/421,917 filed Dec. 10, 2010 (and related Ser. No. 13/303,855, filed Nov. 23, 2011), we have described a hydrocarbon upgrading process comprising (a) treating a first hydrocarbon stream in at least one of a steam cracker, catalytic cracker, coker, hydrocracker, reformer, and the like, under suitable conditions to produce a second stream comprising $C_6$ to $C_{10}+$ aromatic hydrocarbons; (b) dealkylating and/or transalkylating and/or cracking (D/T/C) the second stream by contact with a suitable catalyst under suitable reaction conditions to produce a third stream having an increased benzene and/or toluene content compared with the second stream and a $C_3-$ paraffin by-product; and (c) methylating at least a portion of the third stream with a methylating agent to selectively produce para-xylene. By integrating different upgrading steps, this process offers significant advantages in terms of higher petrochemical yields and lower energy consumption as compared with existing processes for enriching the BTX content of hydrocarbon streams.

Further investigation into the process described in U.S. Application Ser. No. 61/421,917 (and related Ser. No. 13/303,855) has, however, now shown that, by effecting the D/T/C step over a catalyst and under conditions that favor the production of light olefins as well as benzene and/or toluene, the feedstock window (broader carbon number) of the process can be increased, feed preparation can be simplified and hydrogen usage can be reduced. In addition, the process co-produces light ($C_3-$) olefins, which are in high demand in the chemical industry, rather than lower value products, such as LPG.

SUMMARY OF THE INVENTION

Accordingly, the invention resides in one aspect in a hydrocarbon upgrading process comprising:

(a) treating a hydrocarbon feed in at least one of a steam cracker, catalytic cracker, coker, hydrocracker, and reformer under suitable conditions to produce a first stream comprising olefinic and aromatic hydrocarbons;

(b) separating from said first stream a second stream composed mainly of $C_4$ to $C_{12}$ olefinic and aromatic hydrocarbons;

(c) contacting at least part of the second stream with a catalyst in the absence of added hydrogen under reaction conditions including a temperature of about 450° C. to about 700° C. effective to dealkylate, transalkylate, crack, and aromatize components of said second stream to produce a third stream having an increased benzene and/or toluene content compared with said second stream and a $C_3-$ olefin by-product;

(d) recovering the $C_3-$ olefins by-product; and (e) separating a fourth stream comprising toluene from said third stream.

Conveniently, the first hydrocarbon stream is selected from natural gas liquids, natural gas condensate, naphtha, distillate, gas oils, and/or resids.

Conveniently, the catalyst in (c) comprises a molecular sieve having a Constraint Index of less than 3, preferably zeolite Y, and optionally also comprises a molecular sieve having a Constraint Index of about 3 to about 12, preferably an MFI zeolite, in an amount of at least 10 wt % of the zeolite content of said catalyst. Generally, the catalyst is substantially free of hydrogenation metal.

Conveniently, step (c) is carried out in a moving bed reactor, preferably a fluid bed reactor.

Conveniently, wherein part of the catalyst is removed from the reactor and circulated to an oxidative regenerator. Additional fuel may be added to the regenerator to heat the catalyst to provide a portion of the heat of reaction for step (c).

Conveniently, the process further comprises one or more of:

(i) removing $C_4+$ olefins and saturated aliphatics from the third stream and recycling said $C_4+$ olefins and saturated aliphatics to (c);

(ii) removing benzene from the third stream and recycling said benzene to (c); and (iii) removing $C_9+$ aromatics from the third stream and recycling said $C_9+$ aromatics to (b) and/or (c).

In one embodiment, the process further comprises (f) methylating at least part of the fourth stream with a methylating agent, such as methanol, to produce a xylene-enriched $C_8+$ stream.

Conveniently, the process further comprises recovering para-xylene from said xylene-enriched stream to leave a para-xylene-depleted $C_8$ stream, which may be recycled to (b) and/or (c).

Conveniently, the process further comprises removing $C_7$ or $C_6$ and $C_7$ aliphatic hydrocarbons from said third stream or from the fourth stream prior to the methylating (f) and recycling the $C_7$ or $C_6$ and $C_7$ aliphatic hydrocarbons to (b) and/or (c).

BRIEF DESCRIPTION OF THE DRAWINGS

FIG. 1 is a schematic drawing of a hydrocarbon upgrading process according to a first embodiment of the present invention.

DETAILED DESCRIPTION

As used herein, the term "$C_n$" hydrocarbon wherein n is a positive integer, e.g., 1, 2, 3, 4, 5, 6, 7, 8, 9, 10, 11, 12, means a hydrocarbon having n number of carbon atom(s) per molecule. The term "$C_n+$" hydrocarbon wherein n is a positive integer, e.g., 1, 2, 3, 4, 5, 6, 7, 8, 9, 10, 11, 12, as used herein, means a hydrocarbon having at least n number of carbon atom(s) per molecule. The term "$C_n-$" hydrocarbon wherein n is a positive integer, e.g., 1, 2, 3, 4, 5, 6, 7, 8, 9, 10, 11, 12, as used herein, means a hydrocarbon having no more than n number of carbon atom(s) per molecule.

As used herein "resid" refers to the complex mixture of heavy petroleum compounds otherwise known in the art as residuum or residual. Atmospheric resid is the bottoms product produced in atmospheric distillation where the endpoint of the heaviest distilled product is nominally 650° F. (343° C.), and is referred to as 650° F.$^+$ (343° C.$^+$) resid. Vacuum resid is the bottoms product from a column under vacuum where the heaviest distilled product is nominally 1050° F. (566° C.), and is referred to as 1050° F.$^+$ (566° C.$^+$) resid. (The term "nominally" means here that reasonable experts may disagree on the exact cut point for these terms, but probably by no more than +/−50° F. or at most +/−100° F.) The term "resid" as used herein means the 650° F.$^+$ (343° C.$^+$) resid and 1050° F.$^+$ (566° C.$^+$) resid unless otherwise specified (note that 650° F.$^+$ resid comprises 1050° F.$^+$ resid).

Described herein is hydrocarbon upgrading process, in which a hydrocarbon feed is treated in at least one of a steam cracker, catalytic cracker, coker, hydrocracker, and reformer under suitable conditions to produce a first stream enriched in olefinic and/or aromatic hydrocarbons. A second stream composed mainly of $C_4$ to $C_{12}+$ olefinic and aromatic hydrocarbons is separated from the first stream and is fed to a catalytic reactor where the components of the stream undergo dealkylation, transalkylation, cracking and aromatization (DTCA) in the absence of added hydrogen to produce a $C_4+$ third stream having an increased benzene and/or toluene content compared with said second stream and a $C_3-$ olefin by-product. The by-product is recovered and the toluene is separated from the third stream and is optionally methylated by reaction with methanol to produce a xylene-enriched product. Preferably, the methylation is para-selective meaning that para-xylene is produced at greater than equilibrium ratio with respect to ortho-xylene and meta-xylene.

Hydrocarbon Feedstock

Any hydrocarbon composition conventionally fed to a steam cracker, catalytic cracker, coker, hydrocracker, or reformer can be used as the hydrocarbon feed in the present process. Thus, for example, the hydrocarbon feed can comprise a natural gas liquid or condensate, naphtha, gas oil or any distillate fraction of whole crude oil, including in some cases the residual fraction remaining after an atmospheric or vacuum distillation process (e.g. "resid").

Treating the hydrocarbon feed in the steam cracker, catalytic cracker, coker, hydrocracker, or reformer produces a first hydrocarbon stream having a broad spectrum of olefinic and aromatic hydrocarbons depending on the initial composition of the hydrocarbon feed and also on the unit used to process the feed. The first hydrocarbon stream is then subjected to one or more separation operations (such as by distillation column or absorber) to recover $C_3-$ olefins, such as ethylene and propylene, fuel gas and $C_{12}+$ hydrocarbons and leave a second hydrocarbon stream composed mainly of $C_4$ to $C_{12}$ aliphatic and aromatic hydrocarbons. The precise composition of the second hydrocarbon stream will depend on the initial composition of the hydrocarbon feed and on the unit used to process the feed. In fact, depending on the operating targets and efficiency of the fractionation steps used to remove these components, the second hydrocarbon stream may contain quantities (generally less than 20 wt %) of $C_4-$ and $C_{12}+$ hydrocarbons.

In a preferred embodiment of the invention, in which a steam cracker is employed as the process unit, the second hydrocarbon stream is a pyrolysis gasoline containing from about 15 wt % to about 65 wt % benzene, from about 5 wt % to about 35 wt % toluene, from about 1 wt % to about 15 wt % of $C_8+$ aromatic compounds and up to 50 wt %, typically about 1 wt % to about 15 wt %, non-aromatics, the exact composition depending on the composition of the feedstock to the steam cracker, the intensity of the pyrolysis reaction, and the separation and processing scheme for the pygas stream.

In another preferred embodiment of the invention, in which a steam cracker is employed as the process unit, the second hydrocarbon stream is a $C_4$ to $C_{10}$ containing stream which, in one example, has the composition given in Table 1 below:

TABLE 1

| Species | Wt % |
|---|---|
| C4 diolefins | 10.3% |
| C4 olefins | 11.9% |
| C4 saturates | 1.1% |
| C5 cyclo-diolefins | 3.8% |
| C5 diolefins | 4.3% |
| C5 cyclo-olefins | 0.8% |
| C5 cyclo sat's | 0.0% |
| C5 olefins (other) | 2.6% |
| C5 saturates (other) | 1.0% |
| C6 cyclodiolefins | 1.6% |
| C6 cyclo-olefins | 0.3% |
| C6 cyclo-olefins | 2.0% |
| C6 olefins (other) | 0.9% |
| C6 saturates (other) | 0.8% |
| Benzene | 10.7% |
| C7 olefins | 2.4% |
| C7 saturates | 1.6% |
| Toluene | 7.6% |
| C8 olefins | 1.1% |
| C8 saturates | 0.9% |
| Ethylbenzene | 3.2% |
| Xylenes | 3.6% |
| Indanes | 7.8% |
| Isopropylbenzenes | 0.1% |

TABLE 1-continued

| Species | Wt % |
|---|---|
| Propylbenzenes | 0.3% |
| Trimethylbenznes | 1.8% |
| Methylethylbenznes | 3.1% |
| Trimethylcyclohexanes | 0.0% |
| Propylcyclohexanes | 0.1% |
| Butylcyclopentane | 7.3% |
| Nonane | 0.1% |
| Methyloctanes | 0.0% |
| Dimethylheptanes | 0.0% |
| Trimethylhexanes | 0.0% |
| Naphthalene | 2.1% |
| Methylindanes | 1.8% |
| Dimethylethylbenzens | 1.5% |
| Methylpropylbenzens | 0.1% |
| Butylbenzenes | 0.2% |
| Decane | 0.0% |
| Methylnonanes | 0.0% |
| Dimethyloctanes | 0.0% |
| Dicyclopentans | 1.1% |
| Total | 100.0% |

Generally, as the intensity of the pyrolysis reaction increases, which can be noted by the rising outlet temperature of the reactor or by the changing of the ratio of two products, such as propylene and methane, more aromatics will be present in the effluent. Similarly, as weight of the feedstock to the pyrolysis furnace increases, the yield of aromatics in the pygas will also increase. Naphthas and gasoils are conventional feedstocks to steam crackers, including virgin and hydrotreated streams. Resid-containing feeds (typically containing a lesser portion of 1050° F.+ (566° C.+) resid, preferably 20 wt % or less 1050° F.+ (566° C.+) resid, based upon the weight of the feed, preferably 10 wt % or less) can be processed by first passing through the convection section of the steam cracking furnace, then passing to a vapor/liquid separating drum, which can optionally be integrated with the pyrolysis furnace, to drop out the heaviest fraction.

In the current process, in addition to the $C_4$ to $C_{12}$ feed; higher carbon number species, for example $C_{13}$ to $C_{20}+$ material may also be included. While only a portion of these heavier species may convert to higher value high products (light olefins and BTX) and a portion will convert to coke on the catalyst, this might be preferred since the coke can be combusted to help reheat the catalyst to then provide the heat needed for the DTCA reactions. Ideally, the quantity of heavies contained in the feed is such that the DTCA reactor and regenerator are in heat balance.

Dealkylation, Transalkylation, Cracking and Aromatization

The entire $C_4$ to $C_{12}$ second hydrocarbon stream can be supplied to the DTCA reactor, although it may be preferable to remove a $C_6$ and $C_7$ fraction from the second stream prior to feeding the remainder of the second stream to the DTCA reactor. In such an embodiment, the $C_6$ and $C_7$ fraction is then subjected to an aliphatics extraction step, conveniently by solvent extraction or selective adsorption, whereby the aliphatic component of the fraction is removed to leave a benzene and toluene-rich fraction. The benzene and toluene-rich fraction can then be fed to the methylation step described below, either directly or after preliminary hydrodesulfurization, while the aliphatic component is fed to the DTCA reactor.

The DTCA reactor is a catalytic reactor in which part or all of the second hydrocarbon stream is contacted with a catalyst in the absence of added hydrogen under reaction conditions including a temperature of about 450° C. to about 700° C., such as about 550° C. to about 620° C., and a pressure of about 70 to 700 kPaa, such as 200 to 350 kPaa. Steam may also be fed to the reactor, for example, to lower the partial pressure of the hydrocarbon feed.

The DTCA catalyst is normally contained in a moving bed, such as a fluid bed, and typically comprises at least one large pore size molecular sieve having a Constraint Index of less than 3. In this respect, the Constraint Index test is described in U.S. Pat. No. 4,016,218, which is incorporated herein by reference and is measured on the zeolite alone without any treatment to adjust the diffusivity of the catalyst. Preferred large pore molecular sieves are generally those having a pore size in excess of 7 Angstroms (e.g. greater than 7 Angstroms). Examples of suitable large pore molecular sieves include zeolite beta, MCM-22, zeolite Y, ultrastable Y-type zeolites (USY), rare earth exchanged Y-type zeolites (REY), rare earth exchanged ultrastable Y-type zeolites (REUSY), rare earth free Z-21 and Z-2.

Optionally, the DTCA catalyst also includes a medium pore size molecular sieve having a Constraint Index of 3 to about 12 (alternately 4 to 12), as measured on the zeolite alone without any treatment to adjust the diffusivity of the catalyst, in addition to the large pore molecular sieve. The medium pore molecular sieve is typically a mordenite framework inverted (MFI) MFI zeolite, especially ZSM-5. Where the catalyst contains an MFI component, this component is generally present in an amount of at least 10 wt %, such as from 10 wt % to 90 wt %, of the zeolite content of the catalyst. ZSM-5 is preferably phosphorous treated to improve thermal and hydrothermal stability as is well known in the art. Preferred medium pore size zeolites are generally those having a pore size of about 5 to 7 Angstroms, such that the zeolite freely sorbs molecules such as n-hexane, 3-methylpentane, benzene, and p-xylene. Particular examples of suitable medium pore zeolites include ZSM-5, ZSM-11, ZSM-12, ZSM-22, ZSM-23, ZSM-35, ZSM-48, and MCM-22, with ZSM-5 and ZSM-11 being particularly preferred.

In addition to the zeolitic components, the DTCA catalyst normally comprises a binder or matrix material that is resistant to the temperatures and other conditions employed in the reactor and provides the catalyst the shape and mechanical integrity needed by the catalyst for use in the given reactor. Preferably, the catalyst is formulated with the binder or matrix material and spray dried to produce spherical particles suitable for use in a fluid bed reactor.

Suitable binder or matrix materials include active and inactive materials and synthetic or naturally occurring zeolites, as well as inorganic materials such as clays, silica and/or metal oxides such as alumina. The inorganic material may be either naturally occurring, or in the form of gelatinous precipitates or gels including mixtures of silica and metal oxides. Use of a binder or matrix material which itself is catalytically active, may change the conversion and/or selectivity of the catalyst composition. Inactive materials suitably serve as diluents to control the rate of reaction. These catalytically active or inactive materials may include, for example, naturally occurring clays, e.g., bentonite and kaolin, to improve the crush strength of the catalyst composition under commercial operating conditions. Other suitable matrix or binder materials include inorganic oxides selected from the group consisting of silica, alumina, zirconia, titania, thoria, beryllia, magnesia, and combinations thereof, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia.

Typically the DTCA catalyst contains a binder or matrix material in an amount ranging from 20 wt % to 80 wt % of the total catalyst.

Generally, the DTCA catalyst is substantially free of hydrogenation metal (contains less than 1,000 ppm by weight of hydrogenation metal), but may in some cases contain up to 10 ppm by weight of platinum as a CO combustion promoter.

Under the conditions specified above, the DTCA catalyst is effective to dealkylate $C_8+$ single-ring aromatic hydrocarbons having at least one alkyl group containing two or more carbon atoms in the second hydrocarbon stream. Thus, exemplary reactions are cracking of ethyltoluene, ethylxylene and cumene to toluene, xylene and benzene respectively. The cracking is often accompanied by production of ethylene and propylene. In addition, the DTCA catalyst is effective to transalkylate $C_8+$ single-ring aromatic hydrocarbons having at least three methyl groups in the feed. Thus, an exemplary reaction is transalkylation of xylene with benzene to produce toluene. Other reactions include cracking and aromatization of aliphatic hydrocarbons in the feed to produce lower olefins and additional aromatic compounds.

In addition to the desired reactions, the DTCA catalyst effects non-selective conversion of the feed to coke which deposits on the catalyst causing its deactivation. Thus, part of the catalyst is continuously or intermittently removed from the reactor and circulated to an oxidative regenerator, where coke is burnt from the catalyst. Additional fuel is optionally added to the regenerator to heat the catalyst to the required regeneration temperature and to provide a portion of the heat of reaction required for the DTCA step.

The effluent from the DTCA reaction is a third hydrocarbon stream having an increased benzene and/or toluene content compared with the second hydrocarbon stream and a $C_3-$ olefin by-product, which is recovered for use as a chemical feedstock. The third hydrocarbon stream is then fed to a distillation system where at least a toluene-containing fraction is removed from the third hydrocarbon stream and fed to the methylation reactor. In some cases, a benzene-containing fraction is also removed by the distillation system and can be recovered as a product of the process or fed to the methylation reactor together with the toluene-containing fraction. In addition, a $C_4+$ olefins and saturated aliphatics stream may be separated from the third hydrocarbon stream and recycled to the DTCA reactor.

Benzene and/or Toluene Methylation

The toluene and, where applicable, the benzene removed from the third hydrocarbon stream is fed as a fourth hydrocarbon stream to a methylation reactor, normally after hydrotreatment to reduce the level of sulfur therein.

In the methylation reactor, the toluene and benzene in the fourth hydrocarbon stream are methylated, generally with methanol, in the presence of a zeolite catalyst at a temperature between about 500° C. and about 700° C., preferably between about 500° C. and about 600° C., a pressure of between about 1 atmosphere and 1000 psig (100 and 7000 kPa), a weight hourly space velocity of between about 0.5 and 1000, and a molar ratio of toluene to methanol (in the reactor charge) of at least about 0.2, e.g., from about 0.2 to about 20. The process is preferably conducted in the presence of added water such that the molar ratio of water to benzene/toluene+methanol in the feed is between about 0.01 and about 10.

The zeolite catalyst employed in the fourth hydrocarbon stream process is selected to have a Diffusion Parameter for 2,2-dimethylbutane of about 0.1 to 15 $sec^{-1}$, and preferably 0.5 to 10 $sec^{-1}$, when measured at a temperature of 120° C. and a 2,2-dimethylbutane pressure of 60 torr (8 kPa). As used herein, the Diffusion Parameter of a particular porous crystalline material is defined as $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus, for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q, D is the diffusion coefficient (cm$^2$/sec) and r is the crystal radius (cm). Graphical solutions for the plane sheet model are given by J. Crank in "The Mathematics of Diffusion", Oxford University Press, Ely House, London, 1967.

The zeolite employed in the present process is normally a medium-pore size aluminosilicate zeolite. Medium pore zeolites are generally defined as those having a pore size of about 5 to 7 Angstroms, such that the zeolite freely sorbs molecules such as n-hexane, 3-methylpentane, benzene and p-xylene. Another common definition for medium pore zeolites involves the Constraint Index test which is described in U.S. Pat. No. 4,016,218, which is incorporated herein by reference. In this case, medium pore zeolites have a Constraint Index of 3 to 12 (alternately 4 to 12), as measured on the zeolite alone without the introduction of oxide modifiers and prior to any steaming to adjust the diffusivity of the catalyst. Particular examples of suitable medium pore zeolites include ZSM-5, ZSM-11, ZSM-12, ZSM-22, ZSM-23, ZSM-35, ZSM-48, and MCM-22, with ZSM-5 and ZSM-11 being particularly preferred.

The medium pore zeolites described above are preferred for the present alkylation process, even though conventional forms of these zeolites have Diffusion Parameter values in excess of the 0.1-15 sec$^{-1}$ range referred to above. The required diffusivity for the catalyst can be achieved, however, by severely steaming the catalyst so as to effect a controlled reduction in the micropore volume of the catalyst to not less than 50%, and preferably 50-90%, of that of the unsteamed catalyst. Reduction in micropore volume is derived by measuring the n-hexane adsorption capacity of the catalyst, before and after steaming, at 90° C. and 75 torr n-hexane pressure.

Steaming of the zeolite is effected at a temperature of at least about 950° C., preferably about 950° C. to about 1075° C., and most preferably about 1000° C. to about 1050° C. for about 10 minutes to about 10 hours, preferably from 30 minutes to 5 hours.

To effect the desired controlled reduction in diffusivity and micropore volume, it may be desirable to combine the zeolite, prior to steaming, with at least one oxide modifier, preferably selected from oxides of the elements of Groups IIA, IIIA, IIIB, IVA, IVB, VA and VIA of the Periodic Table (IUPAC version). Most preferably, said at least one oxide modifier is selected from oxides of boron, magnesium, calcium, lanthanum and most preferably phosphorus. In some cases, it may be desirable to combine the zeolite with more than one oxide modifier, for example a combination of phosphorus with calcium and/or magnesium, since in this way it may be possible to reduce the steaming severity needed to achieve a target diffusivity value. The total amount of oxide modifier present in the catalyst, as measured on an elemental basis, may be between about 0.05 wt % and about 20 wt %, and preferably is between about 0.1 wt % and about 10 wt %, based on the weight of the final catalyst.

Where the modifier includes phosphorus, incorporation of modifier into the catalyst is conveniently achieved by the methods described in U.S. Pat. Nos. 4,356,338; 5,110,776; 5,231,064; and 5,348,643, the entire disclosures of which are incorporated herein by reference. Treatment with phosphorus-containing compounds can readily be accomplished by contacting the zeolite, either alone or in combination with a binder or matrix material, with a solution of an appropriate phosphorus compound, followed by drying and calcining to convert the phosphorus to its oxide form. Contact with the phosphorus-containing compound is generally conducted at a temperature between about 25° C. and about 125° C. for a time between about 15 minutes and about 20 hours. The concentration of the phosphorus in the contact mixture may be between about 0.01 wt % and about 30 wt %. Suitable phosphorus compounds include, but are not limited to, phosphonic, phosphinous, phosphorus and phosphoric acids, salts and esters of such acids and phosphorous halides.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150° C. to 750° C., preferably about 300° C. to 500° C., for at least 1 hour, preferably 3-5 hours. Similar techniques known in the art can be used to incorporate other modifying oxides into the catalyst employed in the alkylation process.

In addition to the zeolite and modifying oxide, the catalyst employed in the alkylation process may include one or more binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia, and silica-magnesia-zirconia.

The relative proportions of porous crystalline material and inorganic oxide matrix vary widely, with the content of the former ranging from about 1 wt % to about 90 wt % and more usually, particularly when the composite is prepared in the form of beads, in the range of about 2 wt % to about 80 wt % of the composite. Preferably, the matrix material comprises silica or a kaolin clay.

The alkylation catalyst used in the present process may optionally be precoked. The precoking step is preferably carried out by initially utilizing the uncoked catalyst in the toluene methylation reaction, during which coke is deposited on the catalyst surface and thereafter controlled within a desired range, typically from about 1 wt % to about 20 wt % and preferably from about 1 wt % to about 5 wt %, by periodic regeneration by exposure to an oxygen-containing atmosphere at an elevated temperature.

One of the advantages of the catalyst described herein is its ease of regenerability. Thus, after the catalyst accumulates coke as it catalyzes the toluene methylation reaction, it can easily be regenerated by burning off a controlled amount of coke in a partial combustion atmosphere in a regenerator at temperatures in the range of from about 400° C. to about 700° C. The coke loading on the catalyst may thereby be reduced or substantially eliminated in the regenerator. If it is desired to maintain a given degree of coke loading, the regeneration step may be controlled such that the regenerated catalyst returning to the toluene methylation reaction zone is coke-loaded at the desired level.

The present process may suitably be carried out in fixed, moving, or fluid catalyst beds. If it is desired to continuously control the extent of coke loading, moving or fluid bed configurations are preferred. With moving or fluid bed configurations, the extent of coke loading can be controlled by varying the severity and/or the frequency of continuous oxidative regeneration in the catalyst regenerator.

Using the present process, toluene can be alkylated with methanol so as to produce para-xylene at a selectivity of at least about 80 wt % (based on total $C_8$ aromatic product) at a per-pass toluene conversion of at least about 15 wt % and a trimethylbenzene production level less than 1 wt %. The olefin-rich light gas by-product may be recovered in a dedicated olefins recovery unit or routed to a steam cracker olefins recovery section. Unreacted toluene, methanol and a portion of the water product may be recycled to the methylation reactor and heavy byproducts routed to fuels dispositions. The $C_8$ fraction is routed to a para-xylene recovery unit, which typically operates by fractional crystallization or by selective adsorption (e.g., Parex or Eluxyl) to recover a para-xylene product stream from the alkylation effluent and leave a para-xylene-depleted stream containing mainly $C_7$ and $C_8$ hydrocarbons. The para-xylene-depleted stream is conveniently recycled to the DTCA reactor, generally after removal of any toluene for recycle to methylation step.

The invention will now be more particularly described with reference to the accompanying drawing and the following non-limiting Examples.

Referring initially to FIG. 1, a raw $C_4$ to $C_{12}$ aliphatic and aromatic hydrocarbon product from a steam cracker (not shown) is fed by line 11 to a first fractionation system 12, where the product is separated into a first $C_6-$ fraction, a second $C_6$ and $C_7$ fraction and a third $C_8+$ fraction. The first and third fractions are fed by lines 13 and 14 respectively to a DTCA reactor 15, whereas the second fraction is fed by line 16 to an optional aliphatics extraction unit 17. The aliphatic component of the second $C_6$ and $C_7$ fraction is removed by the aliphatics extraction unit 17 and fed by line 18 to the DTCA reactor 15, while the remaining benzene and toluene-rich fraction is fed by line 19 via an optional hydrosulfurization unit 21 to a methylation reactor 22.

The DTCA reactor 15 dealkylates, transalkylates, cracks and aromatizes the various components of the feed to produce a product stream having an increased benzene and/or toluene content compared with feed and a $C_3-$ olefin by-product. The product stream is fed by line 23 back to the first fractionation system 12, while the $C_3-$ olefin by-product is recovered via line 24.

Methanol is fed by line 25 to the methylation reactor 22 to react with the benzene and toluene-rich fraction from the hydrosulfurization unit 21 and produce xylenes together with an olefin-rich light gas. The effluent from the methylation reactor 22 is fed to separator 26 where the light gas is recovered via line 27, while the remainder of the effluent is fed to a second fractionation system 28, where the effluent is divided into an overhead fraction composed mainly of unreacted benzene and toluene, a $C_8+$ bottoms fraction. The overhead fraction is recycled back to the methylation reactor 22 by line 29, whereas the $C_8+$ bottoms fraction is fed by line 31 to a third fractionation system 32.

The $C_8+$ bottoms fraction is divided by the third fractionation system 32 into a $C_9+$ bottoms fraction which is recycled back to the DTCA reactor 15 via line 33 and a $C_8$ fraction which is passed by line 34 to a para-xylene recovery unit 35. Para-xylene is selectively removed from the $C_8$ fraction by the unit 35 to produce a para-xylene product stream, which is recovered via line 36, and a para-xylene-depleted stream which is recycled to the DTCA reactor 15 via line 37.

The DTCA reactor 15 dealkylates, transalkylates, cracks and aromatizes the various components of the feed to produce a product stream having an increased benzene and/or toluene content compared with feed and a $C_3-$ olefin by-product. The product stream is fed to fractionation system 40 where a C4+ stream is recovered and fed by line 23 back to the first fractionation system 12, while the $C_3-$ olefin by-product is recovered via line 24.

This invention further relates to:

1. A hydrocarbon upgrading process comprising:
    (a) treating a hydrocarbon feed in at least one of a steam cracker, catalytic cracker, coker, hydrocracker, and reformer under suitable conditions to produce a first stream comprising olefinic and aromatic hydrocarbons;
    (b) recovering from said first stream a second stream composed mainly of $C_4$ to $C_{12}$ olefinic and aromatic hydrocarbons;
    (c) contacting at least part of the second stream with a catalyst in the absence of added hydrogen under reaction conditions including a temperature of about 450° C. to about 700° C. effective to dealkylate, transalkylate, crack and aromatize components of said second stream to produce a third stream having an increased benzene and/or toluene content compared with said second stream and a $C_3-$ olefin by-product;
    (d) recovering $C_3-$ olefins from said third stream; and
    (e) separating a fourth stream comprising toluene from said third stream.

2. The process of paragraph 1, wherein the first hydrocarbon stream is selected from natural gas liquids, natural gas condensate, naphtha, distillate, gas oils, and/or resids.

3. The process of paragraph 1 or 2, wherein said catalyst comprises a molecular sieve having a Constraint Index of less than 3.

4. The process of paragraph 1 or 2, wherein said catalyst comprises zeolite Y.

5. The process of any of paragraphs 1 to 4, wherein said catalyst also comprises a molecular sieve having a Constraint Index of 3 to about 12 (alternately 4 to 12).

6. The process of any of paragraphs 1 to 5, wherein said catalyst also comprises MFI zeolite.

7. The process of paragraph 6, wherein said MFI zeolite comprises at least 10 wt % of the zeolite content of said catalyst.
8. The process of any of paragraphs 1 to 7, wherein said catalyst is substantially free of hydrogenation metal.
9. The process of any of paragraphs 1 to 8 further comprising removing C$_4$+ olefins and saturated aliphatics from the third stream and recycling said C$_4$+ olefins and saturated aliphatics to (c).
10. The process of any of paragraphs 1 to 9 further comprising removing benzene from the third stream and recycling said benzene to (c).
11. The process of any of paragraphs 1 to 10, wherein said fourth stream also comprises benzene.
12. The process of any of paragraphs 1 to 11 and further comprising removing C$_9$+ aromatics from the third stream and recycling said C$_9$+ aromatics to (b).
13. The process of any of paragraphs 1 to 12, wherein step (c) is carried out in a moving bed reactor, preferably a fluid bed reactor.
14. The process of paragraph 13, wherein part of the catalyst is removed from the reactor and circulated to an oxidative regenerator.
15. The process of paragraph 14, wherein additional fuel is added to the regenerator to heat the catalyst to provide a portion of the heat of reaction for step (c).
16. The process of any of paragraphs 1 to 15 further comprising:
 (f) methylating at least part of the fourth stream with a methylating agent to produce a xylene-enriched C$_8$+ stream.
17. The process of paragraph 16, further comprising hydrotreating said fourth stream prior to the methylating (f).
18. The process of paragraph 16 or 17, wherein said methylating agent is methanol.
19. The process of paragraph 16, 17, or 18, wherein said methylating (f) also produces a C$_3$− olefin by-product which is recovered.
20. The process of any of paragraphs 16 to 19, further comprising removing C$_9$+ hydrocarbons from said xylene-enriched C$_8$+ stream and recycling said C$_9$+ hydrocarbons to (c).
21. The process of any of paragraphs 16 to 20, further comprising recovering para-xylene from said xylene-enriched stream to leave a para-xylene-depleted C$_8$ stream.
22. The process of paragraph 21, further comprising recycling the para-xylene-depleted C$_8$ stream to (c).
23. The process of any of paragraphs 16 to 22, further comprising removing C$_7$ or C$_6$ and C$_7$ aliphatic hydrocarbons from said third stream or from the fourth stream prior to the methylating (f).
24. The process of paragraph 23, further comprising recycling the C$_7$ or C$_6$ and C$_7$ aliphatic hydrocarbons to (c).
25. The process of paragraph 14, further comprising removing C$_7$ or C$_6$ and C$_7$ aliphatic hydrocarbons from said third stream or from the fourth stream prior to the methylating (f), and optionally further comprising recycling the C$_7$ or C$_6$ and C$_7$ aliphatic hydrocarbons to (c).

Example 1

This Example provides the estimated results of employing the process shown in FIG. 1 to upgrade a 1,800 kta of the C$_4$ to C$_{10}$ steam cracked naphtha feed shown in Table 1 above. The C$_3$− olefin by-product recovered via line 24 was composed of 220 kta of ethylene, 430 kta propylene, and 110 kta of saturates. After passage through the hydrosulfurization unit 21 the methylation feed in line 29 was composed of 210 kta of benzene and 980 kta of toluene. The methanol feed to the methylation reactor was 760 kta. The light gas recovered via line 27 was composed of 90 kta of ethylene and 50 kta of propylene. The para-xylene product recovered via line 36 was 1,180 kta.

All documents described herein are incorporated by reference herein, including any priority documents and/or testing procedures to the extent they are not inconsistent with this text, provided however that any priority document not named in the initially filed application or filing documents is not incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa. Thus, the term "comprising" encompasses the terms "consisting essentially of," "is," and "consisting of" and anyplace "comprising" is used "consisting essentially of," "is," or consisting of may be substituted therefor.

What is claimed is:
1. A hydrocarbon upgrading process comprising:
 (a) treating a hydrocarbon feed in at least one of a steam cracker, catalytic cracker, coker, hydrocracker, and reformer under suitable conditions to produce a first stream comprising olefinic and aromatic hydrocarbons;
 (b) recovering from said first stream a second stream composed mainly of C$_4$ to C$_{12}$ olefinic and aromatic hydrocarbons and less than 20 wt % of C$_4$− and C$_{12}$+ hydrocarbons;
 (c) contacting at least part of the second stream with a catalyst in the absence of added hydrogen under reaction conditions including a temperature of about 450° C. to about 700° C. effective to dealkylate, transalkylate, crack and aromatize components of said second stream to produce a third stream having an increased benzene and/or toluene content compared with said second stream and a C$_3$− olefin by-product;
 (d) recovering C$_3$− olefins from said third stream;
 (e) separating a fourth stream comprising toluene from said third stream; and
 (f) methylating at least part of the fourth stream with a methylating agent to produce a xylene-enriched C$_8$+ stream.
2. The process of claim 1, wherein the first hydrocarbon stream is selected from natural gas liquids, natural gas condensate, naphtha, distillate, gas oils, and/or resids.
3. The process of claim 1, wherein said catalyst comprises a molecular sieve having a Constraint Index of less than 3.
4. The process of claim 1, wherein said catalyst comprises zeolite Y.
5. The process of claim 1, wherein said catalyst comprises 1) a molecular sieve having a Constraint Index of less than 3; and 2) a molecular sieve having a Constraint Index of 3 to about 12.
6. The process of claim 1, wherein said catalyst comprises: 1) zeolite Y and 2) a mordenite framework inverted, MFI, zeolite.

7. The process of claim 6, wherein said MFI zeolite comprises at least 10 wt % of the zeolite content of said catalyst.

8. The process of claim 1, wherein said catalyst is substantially free of hydrogenation metal.

9. The process of claim 1, further comprising removing $C_4+$ olefins and saturated aliphatics from the third stream and recycling said $C_4+$ olefins and saturated aliphatics to (c).

10. The process of claim 1, further comprising removing benzene from the third stream and recycling said benzene to (c).

11. The process of claim 1, wherein said fourth stream also comprises benzene.

12. The process of claim 1 further comprising removing $C_9+$ aromatics from the third stream and recycling said $C_9+$ aromatics to (b) and/or (c).

13. The process of claim 1, wherein step (c) is carried out in a moving bed reactor.

14. The process of claim 13, wherein part of the catalyst is removed from the reactor and circulated to an oxidative regenerator.

15. The process of claim 14, wherein additional fuel is added to the regenerator to heat the catalyst to provide a portion of the heat of reaction for step (c).

16. The process of claim 1, wherein the methylation is conducted in the presence of added water such that the molar ratio of water to benzene/toluene+methanol in the feed is between about 0.01 and about 10.

17. The process of claim 1, further comprising hydrotreating said fourth stream prior to the methylating (f).

18. The process of claim 1, wherein said methylating agent is methanol.

19. The process of claim 1, wherein said methylating (f) also produces a $C_3-$ olefin by-product which is recovered.

20. The process of claim 1, further comprising removing $C_9+$ hydrocarbons from said xylene-enriched $C_8+$ stream and recycling said $C_9+$ hydrocarbons to (c).

21. The process of claim 1, further comprising recovering para-xylene from said xylene-enriched stream to leave a para-xylene-depleted $C_8$ stream.

22. The process of claim 21, further comprising recycling the para-xylene-depleted $C_8$ stream to (c).

23. The process of claim 1, further comprising removing $C_7$ or $C_6$ and $C_7$ aliphatic hydrocarbons from said third stream or from the fourth stream prior to the methylating (f).

24. The process of claim 23, further comprising recycling the $C_7$ or $C_6$ and $C_7$ aliphatic hydrocarbons to (c).

25. The process of claim 1, wherein step (c) is carried out in a fluid bed reactor.

26. The process of claim 1 wherein the methylation is conducted in the presence of an aluminosilicate zeolite having a pore size of about 5 to 7 Angstroms, where the aluminosilicate zeolite is steamed so as to effect a reduction in the micropore volume of the aluminosilicate zeolite to not less than 50% of that of the unsteamed aluminosilicate zeolite.

27. The process of claim 26 wherein the aluminosilicate zeolite includes ZSM-5, ZSM-11, ZSM-12, ZSM-22, ZSM-23, ZSM-35, ZSM-48, or MCM-22.

28. The process of claim 26 wherein the steaming is effected at a temperature of at least about 950° C. for about 10 minutes to about 10 hours.

\* \* \* \* \*